US012802214B2

(12) United States Patent
Masumoto et al.

(10) Patent No.: US 12,802,214 B2
(45) Date of Patent: Nov. 17, 2026

(54) MEDICAL IMAGE DIAGNOSIS SYSTEM, MEDICAL IMAGE DIAGNOSIS METHOD, AND PROGRAM

(71) Applicant: FUJIFILM Corporation, Tokyo (JP)

(72) Inventors: Jun Masumoto, Tokyo (JP); Masaharu Morita, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 257 days.

(21) Appl. No.: 18/533,059

(22) Filed: Dec. 7, 2023

(65) Prior Publication Data

US 2024/0112339 A1 Apr. 4, 2024

Related U.S. Application Data

(63) Continuation of application No. PCT/JP2022/021219, filed on May 24, 2022.

(30) Foreign Application Priority Data

Jun. 17, 2021 (JP) ................................ 2021-100610

(51) Int. Cl.
*G16H 50/20* (2018.01)
*G06T 7/00* (2017.01)
*G16H 30/40* (2018.01)

(52) U.S. Cl.
CPC ........... *G06T 7/0012* (2013.01); *G16H 30/40* (2018.01); *G16H 50/20* (2018.01)

(58) Field of Classification Search
CPC ....... G06T 7/0012; G16H 50/20; G16H 30/40
See application file for complete search history.

(56) References Cited

U.S. PATENT DOCUMENTS 5,807,256 A 9/1998 Taguchi et al.
2019/0125306 A1* 5/2019 Oh ........................ G16H 50/20
(Continued)

FOREIGN PATENT DOCUMENTS

JP S62194581 8/1987
JP 2006340835 12/2006
(Continued)

OTHER PUBLICATIONS

"International Search Report (Form PCT/ISA/210) of PCT/JP2022/021219", mailed on Jul. 5, 2022, with English translation thereof, pp. 1-5.

(Continued)

*Primary Examiner* — Christopher S Kelley
(74) *Attorney, Agent, or Firm* — JCIPRNET

(57) ABSTRACT

Provided are a medical image diagnosis system, a medical image diagnosis method, and a program which reduce a burden on a doctor in a case of performing image diagnosis on a large number of medical images, such as a health checkup. The problem is solved by a medical image diagnosis system including at least one processor, and at least one memory that stores a command to be executed by the at least one processor, in which the at least one processor performs first determination of determining presence or absence of an abnormality from a medical image obtained by imaging a subject, and performs second determination of determining whether or not the medical image is normal in a case in which it is determined that the abnormality is absent in the first determination.

9 Claims, 7 Drawing Sheets

(56) References Cited

U.S. PATENT DOCUMENTS

| | | | |
|---|---|---|---|
| 2020/0202103 A1 | 6/2020 | Tang et al. | |
| 2020/0372641 A1 | 11/2020 | Kim et al. | |
| 2022/0199256 A1* | 6/2022 | Yamada | G06F 18/2113 |
| 2022/0358640 A1* | 11/2022 | Sakashita | A61B 3/0025 |
| 2023/0005251 A1 | 1/2023 | Take et al. | |
| 2024/0212137 A1* | 6/2024 | Meyer | G06T 7/0012 |

FOREIGN PATENT DOCUMENTS

| | | |
|---|---|---|
| JP | 2012026982 | 2/2012 |
| JP | 2019067069 | 4/2019 |
| JP | 6885517 | 6/2021 |
| WO | 2021067624 | 4/2021 |

OTHER PUBLICATIONS

"Written Opinion of the International Searching Authority (Form PCT/ISA/237) of PCT/ JP2022/021219", mailed on Jul. 5, 2022, with English translation thereof, pp. 1-8.
"Office Action of Japan Counterpart Application", issued on Aug. 6, 2025, with English translation thereof, p. 1-p. 10.
"Search Report of Europe Counterpart Application", issued on Sep. 11, 2024, pp. 1-7.
"Notice of Reasons for Refusal of Japan Counterpart Application", issued on Jun. 10, 2026, with English translation thereof, p. 1-p. 6.

* cited by examiner

MEDICAL IMAGE DIAGNOSIS SYSTEM, MEDICAL IMAGE DIAGNOSIS METHOD, AND PROGRAM

CROSS-REFERENCE TO RELATED APPLICATIONS

The present application is a Continuation of PCT International Application No. PCT/JP2022/0021219 filed on May 24, 2022 claiming priority under 35 U.S.C § 119(a) to Japanese Patent Application No. 2021-100610 filed on Jun. 17, 2021. Each of the above applications is hereby expressly incorporated by reference, in its entirety, into the present application.

BACKGROUND OF THE INVENTION

1. Field of the Invention

The present invention relates to a medical image diagnosis system, a medical image diagnosis method, and a program, and particularly, to a technology for diagnosing a medical image.

2. Description of the Related Art

A system that finds and diagnoses an abnormal region in a medical image by using artificial intelligence (AI) is known.

For example, JP2006-340835A discloses a medical image processing system that provides only detection information on an abnormal shadow candidate suspected to be a true positive abnormal shadow and/or an abnormal shadow candidate with low visibility regarding the abnormal shadow candidates detected from the medical images, and that prevents oversight of doctors and improves the efficiency of image interpretation work.

SUMMARY OF THE INVENTION

For health management, a health checkup is performed to examine a health state of a subject. In the health checkup, the subject is mainly a healthy person, and the purpose of diagnosis, a target organ, and a target illness are limited. For regions with possible abnormalities in medical images obtained by the health checkup, it is necessary for a doctor to determine whether there are indeed abnormalities, diagnose possible disease names, and create detailed reports, and these tasks are important.

On the other hand, the doctor also has to confirm the image with no abnormal region. For example, in a case of a health checkup mainly for young people, since a patient with an abnormality is unlikely to be present, a doctor has to confirm a large number of "images with no abnormalities", which is a heavy burden on the doctor.

In contrast, it is conceivable to perform image diagnosis by using lesion detection AI. However, the lesion detection AI is usually created only for a specific disease, and since the types of diseases are enormous, it is difficult to create AI corresponding to all diseases. In addition, the amount of training data is small for rare diseases, and it is difficult to create lesion detection AI. Furthermore, a doctor is responsible for diagnosing unknown diseases for which lesion detection AI cannot be created in the first place. As described above, even in a case in which the number of lesion detection AIs is increased and the accuracy of each lesion detection AI is increased, there is a problem that the final diagnostic accuracy is limited.

The present invention has been made in view of such circumstances, and an object of the present invention is to provide a medical image diagnosis system, a medical image diagnosis method, and a program that reduce a burden on a doctor in a case of performing image diagnosis on a large number of medical images, such as a health checkup.

One aspect of a medical image diagnosis system for achieving the object described above is a medical image diagnosis system comprising at least one processor, and at least one memory that stores a command to be executed by the at least one processor, in which the at least one processor performs first determination of determining presence or absence of an abnormality from a medical image obtained by imaging a subject, and performs second determination of determining whether or not the medical image is normal in a case in which it is determined that the abnormality is absent in the first determination. The abnormality includes, for example, at least one of a disease, an illness, or a lesion. In addition, a case in which the medical image is normal is, for example, a case in which the medical image can be said to be an image of a healthy person. The healthy person refers to a person who is healthy, for example, a person who does not have a disease, an illness, or a lesion. According to the present aspect, it is possible to reduce the burden on the doctors in a case in which the image diagnosis is performed on a large number of medical images.

It is preferable that, for a first case in which it is determined that the abnormality is present in the first determination, a second case in which it is determined that the abnormality is absent in the first determination and it is determined that the medical image is not normal in the second determination, and a third case in which it is determined that the abnormality is absent in the first determination and it is determined that the medical image is normal in the second determination, the at least one processor displays a diagnosis result of the medical image on a display differently for the third case than for the first and second cases.

It is preferable that the at least one processor displays the diagnosis result of the medical image on the display differently between the first case and the second case.

It is preferable that the at least one processor performs different types of post-processing on the medical image for the third case than for the first and second cases.

It is preferable that the at least one processor performs the first determination and the second determination for each organ of the subject from the medical image.

It is preferable that the at least one processor performs third determination of determining the presence or absence of the abnormality from the medical image in a case in which it is determined that the medical image is not normal in the second determination, and the third determination is performed with a sensitivity relatively higher than a sensitivity in the first determination.

It is preferable that the at least one processor performs the first determination by using a first trained model that outputs the abnormality of the medical image in a case in which the medical image is input.

It is preferable that the at least one processor performs the second determination by using a second trained model that outputs whether or not the medical image is normal in a case in which the medical image is input.

It is preferable that the second trained model outputs a probability that the input medical image is normal. The second trained model may output a probability that the input medical image is not normal.

It is preferable that the second trained model is a trained model that has been trained by using combinations of a normal medical image, an abnormal medical image, and labels indicating whether or not the medical image is normal, as a training data set.

Another aspect of a medical image diagnosis method for achieving the object described above is a medical image diagnosis method comprising a first determination step of determining presence or absence of an abnormality from a medical image obtained by imaging a subject, and a second determination step of determining whether or not the medical image is normal in a case in which it is determined that the abnormality is absent in the first determination step. According to the present aspect, it is possible to reduce the burden on the doctors in a case in which the image diagnosis is performed on a large number of medical images.

Still another aspect of a program for achieving the object described above is a program for causing a computer to execute the medical image diagnosis method described above. A computer-readable non-transitory storage medium on which the program is recorded may also be included in the present aspect.

According to the present invention, it is possible to reduce the burden on the doctors in a case in which the image diagnosis is performed on a large number of medical images.

DESCRIPTION OF THE PREFERRED EMBODIMENTS

Hereinafter, a preferred embodiment of the present invention will be described in accordance with the accompanying drawings.

[Configuration of Medical Image Diagnosis System] The medical image diagnosis system according to the present embodiment reduces a burden on a doctor in a case of performing image diagnosis on a large number of medical images, such as a health checkup.

Figure 1:
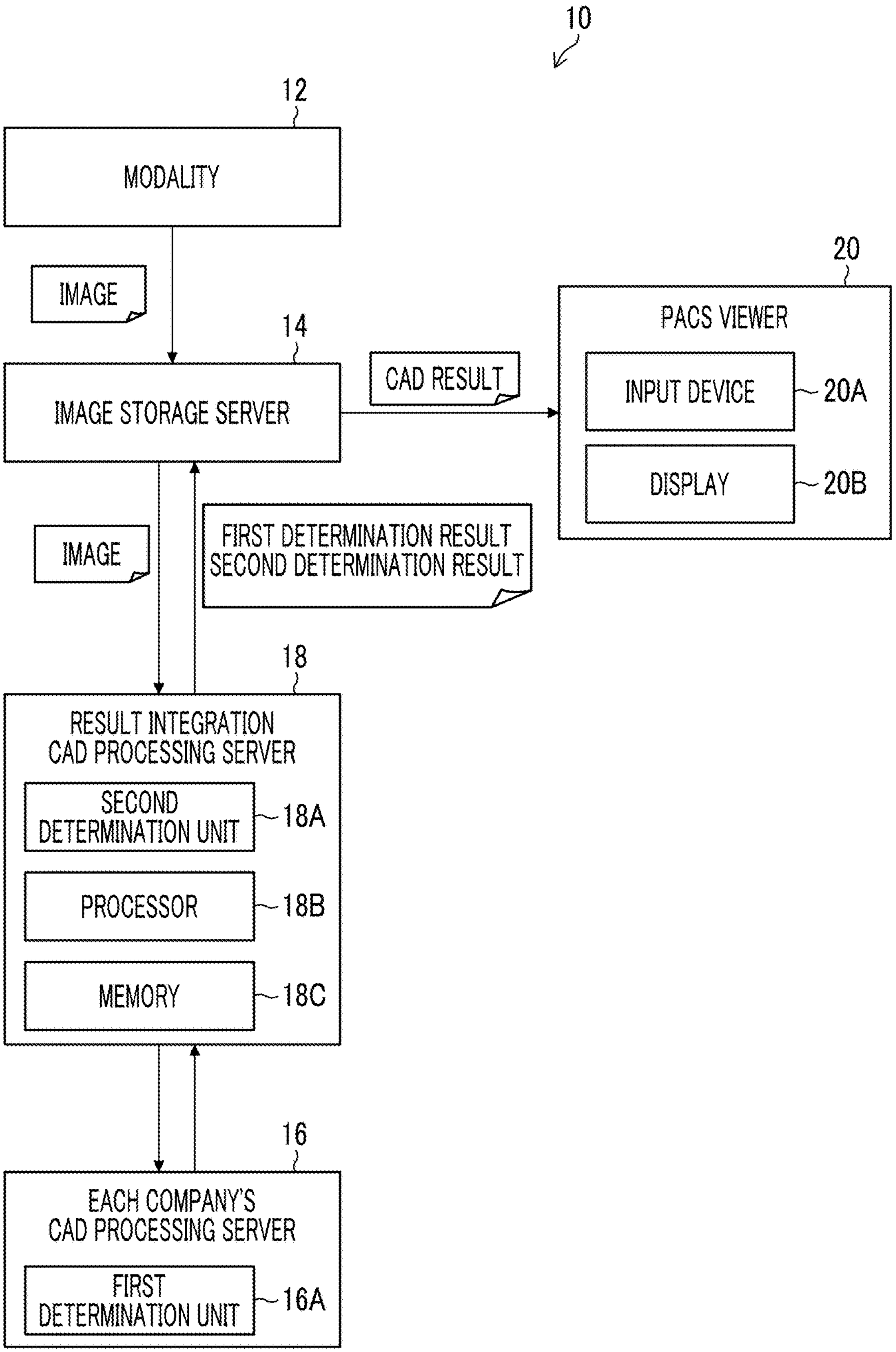
FIG. 1 is a block diagram illustrating a medical image diagnosis system according to the present embodiment.

FIG. 1 is a block diagram illustrating a medical image diagnosis system 10 according to the present embodiment. As illustrated in FIG. 1, the medical image diagnosis system 10 comprises a modality 12, an image storage server 14, each company's computer-aided diagnosis (CAD) processing server 16, a result integration CAD processing server 18, and a picture archiving and communication system (PACS) viewer 20.

The modality 12, the image storage server 14, each company's CAD processing server 16, the result integration CAD processing server 18, and the PACS viewer 20 are each connected to a communication network such as the Internet so that the data can be transmitted and received.

The modality 12 is an imaging apparatus that images an examination target part of a subject and generates a medical image. The modality 12 includes, for example, at least one of an X-ray imaging apparatus, a computed tomography (CT) apparatus, a magnetic resonance imaging (MRI) apparatus, a positron emission tomography (PET) apparatus, an ultrasound apparatus, or a computed radiography (CR) apparatus using a planar X-ray detector.

The image storage server 14 is a server that manages the medical image captured by the modality 12. A computer comprising a large-capacity storage device is applied to the image storage server 14. Software providing a function of a database storage system is incorporated in the computer. The image storage server 14 acquires a medical image captured by the modality 12 and stores the medical image in the large-capacity storage device.

The digital imaging and communications in medicine (DICOM) standard can be applied to the format of the medical image. DICOM tag information defined by the DICOM standard may be added to the medical image. The term "image" in the present specification can include the meaning of image data, which is a signal representing an image, in addition to the meaning of an image itself such as a photograph.

Each company's CAD processing server 16 is composed of a plurality of CAD processing servers owned by a plurality of companies. Each company's CAD processing server 16 may be a single CAD processing server. Each company's CAD processing server 16 includes a first determination unit 16A. The first determination unit 16A includes a program that performs abnormality detection processing for each organ on the medical image acquired from the image storage server 14 and performs first determination to determine the presence or absence of one or more abnormalities from the medical image. The abnormality includes, for example, at least one of a disease, an illness, or a lesion. The first determination result of the first determination unit 16A is associated with the medical image in the image storage server 14 and is stored in the large-capacity storage device.

The first determination unit 16A may be provided in the result integration CAD processing server 18.

The result integration CAD processing server 18 acquires the first determination result from the first determination unit 16A and integrates the first determination result. Here, for example, the CAD results of different types of diseases, illnesses, and lesions for the same organ of the same input image are integrated for a second determination unit 18A. In addition, the result integration CAD processing server 18 includes a second determination unit 18A. For the medical image which is acquired from the image storage server 14 and is determined to have no abnormality by the first determination unit 16A, the second determination unit 18A performs normal determination processing that determines whether or not a medical image is normal for each organ. Whether or not the medical image is normal is, for example, whether or not the medical image can be said to be an image of a healthy person. The healthy person refers to a person who is healthy, for example, a person who does not have a disease, an illness, or a lesion. A second determination result of the second determination unit 18A is associated with the medical image in the image storage server 14 and is stored in the large-capacity storage device.

A personal computer or a workstation is applied to the result integration CAD processing server 18. The result integration CAD processing server 18 comprises a processor 18B and a memory 18C. The processor 18B performs a command stored in the memory 18C.

A hardware structure of the processor 18B includes various processors to be described below. The various processors include a central processing unit (CPU) that is a general-purpose processor actioning as various functional units by executing software (program), a graphics processing unit (GPU) that is a processor specially designed for image processing, a programmable logic device (PLD) such as a field programmable gate array (FPGA) that is a processor having a circuit configuration changeable after manufacturing, and a dedicated electric circuit or the like such as an application specific integrated circuit (ASIC) that is a processor having a circuit configuration dedicatedly designed to execute a specific type of processing.

One processing unit may be configured by one processor among these various processors, or may be configured by two or more same or different kinds of processors (for example, a combination of a plurality of FPGAs, a combination of the CPU and the FPGA, or a combination of the CPU and GPU). In addition, a plurality of functional units may be formed of one processor. As an example of configuring the plurality of functional units with one processor, first, as represented by a computer such as a client or a server, a form of configuring one processor with a combination of one or more CPUs and software and causing the processor to act as the plurality of functional units is present. Second, as represented by a system on chip (SoC) or the like, a form of using a processor that implements the function of the entire system including the plurality of functional units using one integrated circuit (IC) chip is present. Accordingly, various functional units are configured using one or more of the various processors as a hardware structure.

Furthermore, the hardware structure of the various processors is more specifically an electric circuit (circuitry) in which circuit elements such as semiconductor elements are combined.

The memory 18C stores a command to be executed by the processor 18B. The memory 18C includes a random access memory (RAM) and a read only memory (ROM), which are not illustrated. The processor 18B uses the RAM as a work region to execute software using various programs and parameters including a medical image processing program stored in the ROM, and executes various types of processing of the result integration CAD processing server 18 by using the parameters stored in the ROM.

The PACS viewer 20 is a terminal device used by a user, such as a doctor, and, for example, a known image viewer for image interpretation is applied. The PACS viewer 20 may be a personal computer, a workstation, or a tablet terminal.

The PACS viewer 20 comprises an input device 20A and a display 20B. The input device 20A includes a pointing device, such as a mouse, and an input device, such as a keyboard. The user can input an instruction to the medical image diagnosis system 10 using the input device 20A. The display 20B displays a screen necessary for an operation of the input device 20A, and functions as a part for implementing a graphical user interface (GUI). The medical image captured by the modality 12 is displayed on the display 20B. In addition, the first determination result and the second determination result are displayed on the display 20B as CAD results. A touch panel display in which the input device 20A and the display 20B are integrated may be applied to the PACS viewer 20.

Figure 2:
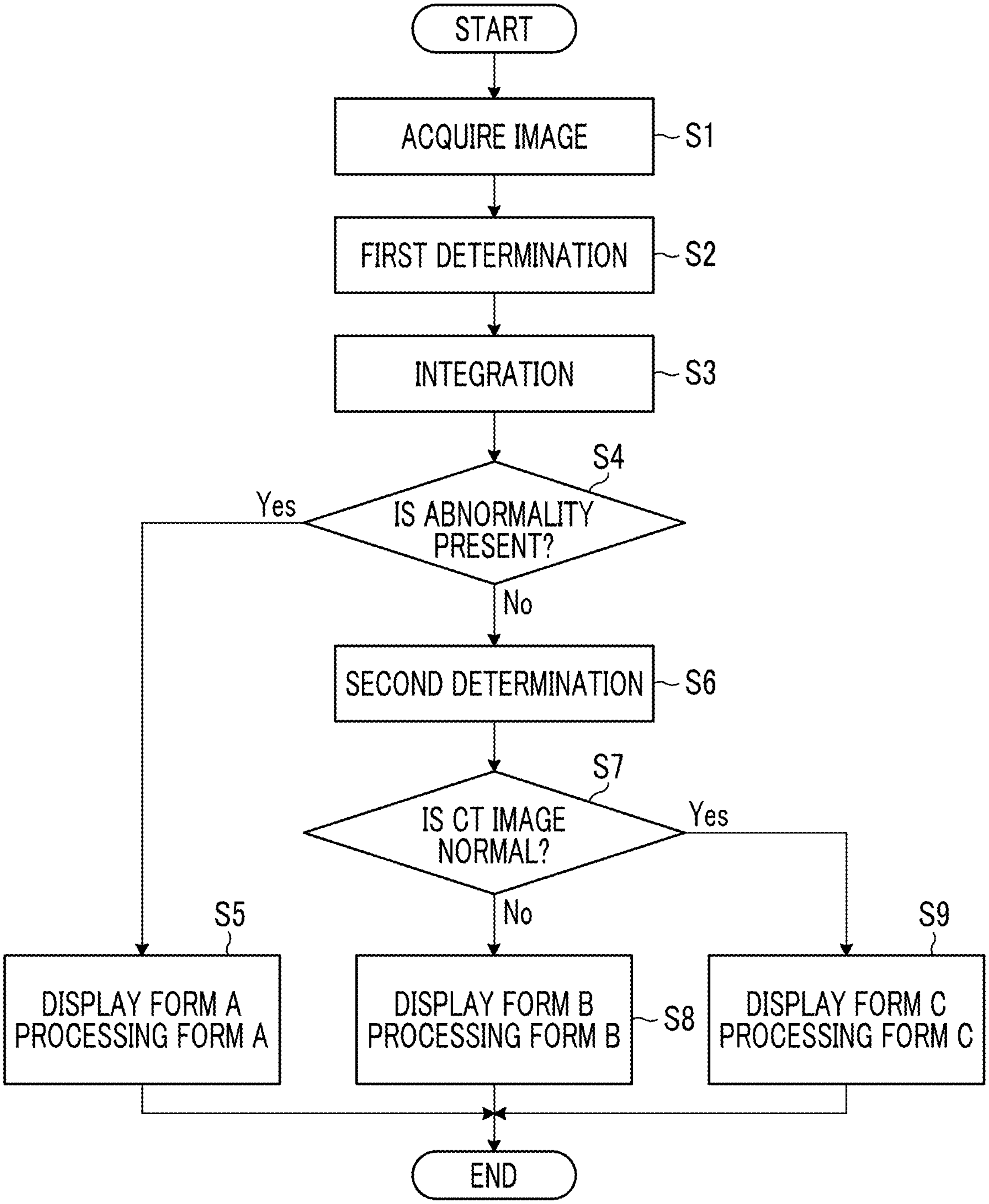
FIG. 2 is a flowchart illustrating a medical image diagnosis method.
Figure 3:
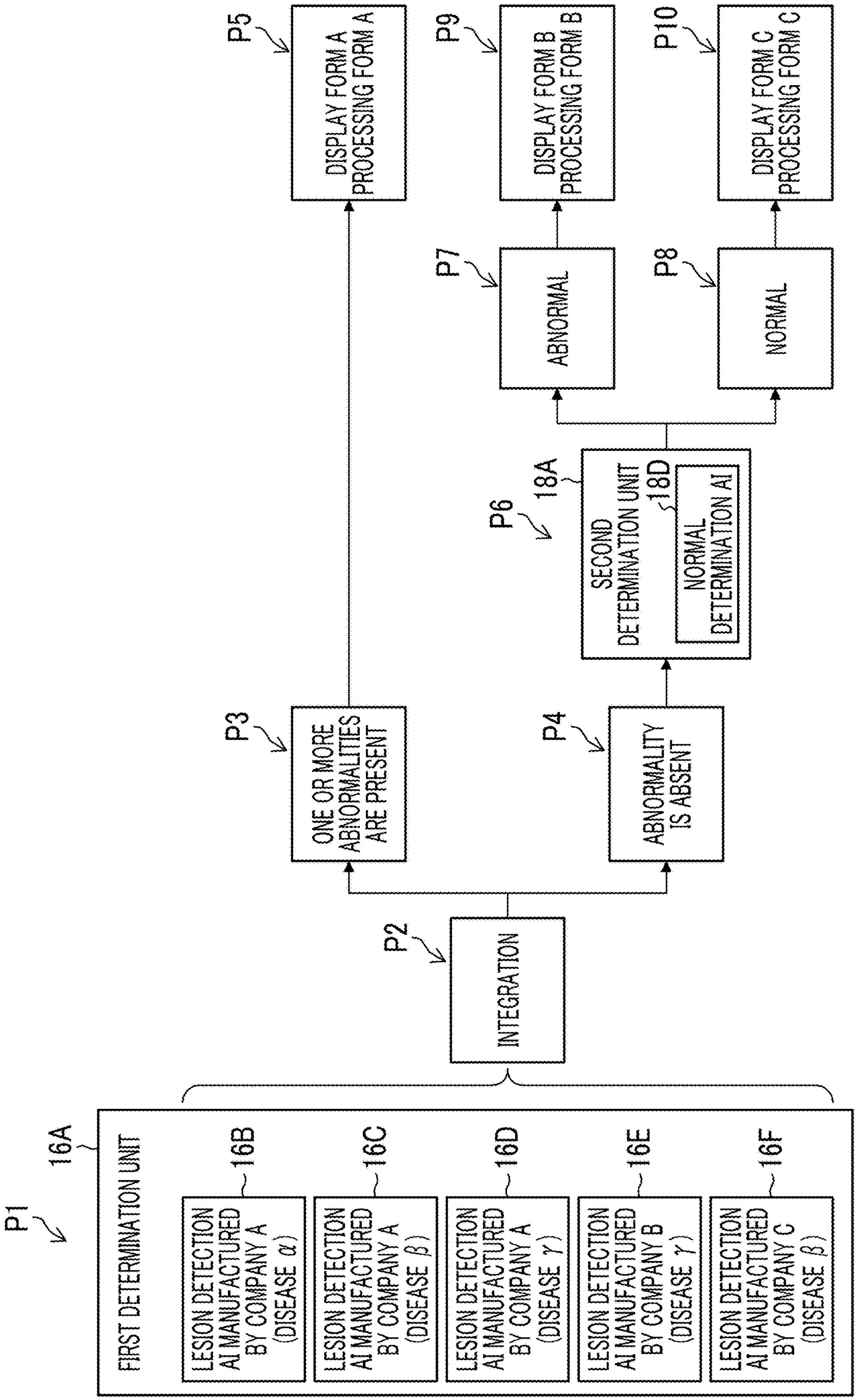
FIG. 3 is a process diagram illustrating the medical image diagnosis method.

[Medical Image Diagnosis Method] FIG. 2 is a flowchart illustrating a medical image diagnosis method using the medical image diagnosis system 10. In addition, FIG. 3 is a process diagram illustrating the medical image diagnosis method. The medical image diagnosis method is implemented by the processor 18B executing the medical image diagnosis program stored in the memory 18C. The medical image diagnosis program may be provided by a computer-readable non-transitory storage medium. In this case, the result integration CAD processing server 18 may read the medical image diagnosis program from the non-transitory storage medium and store the medical image diagnosis program in the memory 18C.

The medical image diagnosis method is performed for each organ of the subject. Here, as an example, a case of diagnosing a CT image of a lung will be described.

In Step S1, the processor 18B of the result integration CAD processing server 18 causes the image storage server 14 to acquire a CT image of a lung of the subject captured by the modality 12. The image storage server 14 acquires the CT image captured by the modality 12.

In Step S2 (an example of a "first determination step"), the processor 18B inputs the CT image acquired by the image storage server 14 to each company's CAD processing server 16. Each company's CAD processing server 16 inputs the CT image to the first determination unit 16A and performs the first determination (Process P1).

As illustrated in FIG. 3, the first determination unit 16A includes a lesion detection AI 16B manufactured by Company A that detects a disease α, a lesion detection AI 16C manufactured by Company A that detects a disease β, a lesion detection AI 16D manufactured by Company A that detects a disease γ, a lesion detection AI 16E manufactured by Company B that detects the disease γ, and a lesion detection AI 16F manufactured by Company C that detects the disease β. For example, the disease α is lung cancer, the disease β is pneumonia, and the disease γ is pneumothorax.

Each of the lesion detection AIs 16B to 16F is a trained model (an example of a "first trained model") that outputs a region of a disease (a lesion region, an example of "abnormality") in a CT image in a case in which the CT image of the lung is input, and each includes a convolutional neural network. Each of the lesion detection AIs 16B to 16F is generated by performing deep learning using a label image in which a doctor labels a region of each disease on the CT image of the lung as training data.

Each of the lesion detection AIs 16B to 16F is set to obtain the probability of each disease for each pixel of the CT image, and a pixel exceeding a predetermined threshold value is considered as the region of the disease. Each of the lesion detection AIs 16B to 16F has a higher specificity compared to a case in which lesion detection is performed independently, that is, a relatively high threshold value is set. As a result, each of the lesion detection AIs 16B to 16F detects a location that is more likely to be a lesion. This is because there are few abnormalities in the health checkup or the like, and even in a case of overlooking, it is possible to determine that the image is abnormal by the second determination of the second determination unit 18A. The lesion detection AI is not limited to the method of obtaining the probability of the disease of each pixel as described above, and may be designed to extract a lesion candidate region in an image in a rectangular shape and output a lesion probability for the rectangular region, for example.

The first determination unit 16A inputs the CT image to each of the lesion detection AIs 16B to 16F. Each of the lesion detection AIs 16B to 16F performs lesion detection processing on the CT image and outputs it as a first determination result.

In Step S3, the processor 18B acquires the first determination result from the first determination unit 16A and integrates the first determination result (Process P2). As for the integration, the description will be omitted since it is the same as described above.

In Step S4, the processor 18B determines whether or not an abnormality (here, a lesion) is present in the CT image from the integrated first determination result. Here, in a case in which one or more lesions are detected by any of the lesion detection AIs 16B to 16F, it is determined that "the abnormality is present". In a case in which the abnormality is present in the CT image (an example of a "first case", Process P3), the processing proceeds to Step S5, and in a case in which the abnormality is absent in the CT image (Process P4), the processing proceeds to Step S6.

In Step S5, the processor 18B causes the display 20B of the PACS viewer 20 to display the CT image in which the abnormality is present in a display form A, and post-processing of a processing form A is performed to make the doctor clearly recognize that the abnormality is present in the CT image in the "first determination result" ("first case") (Process P5). Furthermore, the processor 18B gives accessory information of "type A" to the CT image, stores it in the image storage server 14, and ends the processing of the present flowchart.

In Step S6 (an example of a "second determination step"), the processor 18B inputs the CT image in which an abnormality is absent to the second determination unit 18A. As illustrated in FIG. 3, the second determination unit 18A includes a normal determination AI 18D that determines whether or not the medical image is normal.

The normal determination AI 18D is a trained model (an example of a "second trained model") that determines, in a case in which the CT image of the lung is input, whether or not the CT image is normal, and includes a convolutional neural network. The normal determination AI 18D is generated by deep learning using a training data set of a normal CT image and a normal label and a training data set of an abnormal CT image and an abnormal label. The normal CT image is a CT image of a healthy person. In addition, the abnormal CT image is a CT image having some abnormality, and is, for example, a CT image of a person having at least one of a disease, an illness, or a lesion.

The normal determination AI 18D is generated to output a degree of normality of the input CT image as a numerical value (a score, an example of a "probability"). The normal determination AI 18D outputs that the CT image is not normal in a case in which the degree of normality of the CT image is less than a predetermined threshold value, and outputs that the CT image is normal in a case in which the degree of normality of the CT image is equal to or greater than the threshold value. The second determination unit 18A inputs the CT image to the normal determination AI 18D and acquires a second determination result (Process P6).

In Step S7, the processor 18B determines whether or not the CT image is normal from the second determination result. In a case in which the CT image is not normal (an example of a "second case", Process P7), the processing proceeds to Step S8, and in a case in which the CT image is normal (an example of a "third case", Process P8), the processing proceeds to Step S9.

In Step S8, the processor 18B causes the display 20B of the PACS viewer 20 to display the CT image that is not normal in a display form B, and unlike in the "first case", post-processing of a processing form B is performed to make the doctor clearly recognize that the abnormality is absent in the CT image in the "first determination result" and that the abnormality is present in the CT image in the "second determination result" ("second case") (Process P9). Furthermore, the processor 18B gives accessory information of "type B" to the CT image, stores it in the image storage server 14, and ends the processing of the present flowchart.

On the other hand, in Step S9, the processor 18B causes the display 20B of the PACS viewer 20 to display the normal CT image in the display form C, and performs post-processing of the processing form C so that the doctor can more simply process the "normal CT image" (Process P10). Furthermore, the processor 18B gives accessory information of "type C" to the CT image, stores it in the image storage server 14, and ends the processing of the present flowchart.

The processor 18B causes the display 20B to display the diagnosis results by the "first determination result" and the "second determination result" differently between the display form A and the display form B, and the display form C. The processor 18B may cause the display 20B to display the diagnosis result differently between the display form A and the display form B.

Since the respective diagnosis results of the "first determination result" and the "second determination result" are clearly known to the doctor, it is possible to display different diagnosis results by different display items, description contents, or display forms in the display formats (characters, drawings, colors, or the like). For example, in the display form A, the name of the detected lesion and the region thereof are displayed in a visually recognizable manner in the same manner as in general CAD. In addition, in the display form B, the doctor is notified that the lesion is not detected but is not clearly normal. Furthermore, in the display form C, the fact that there is a high probability that there is no abnormality is presented, the doctor's confirmation is skipped, and the fact that there is no abnormality is automatically reported to the patient.

Figure 4:
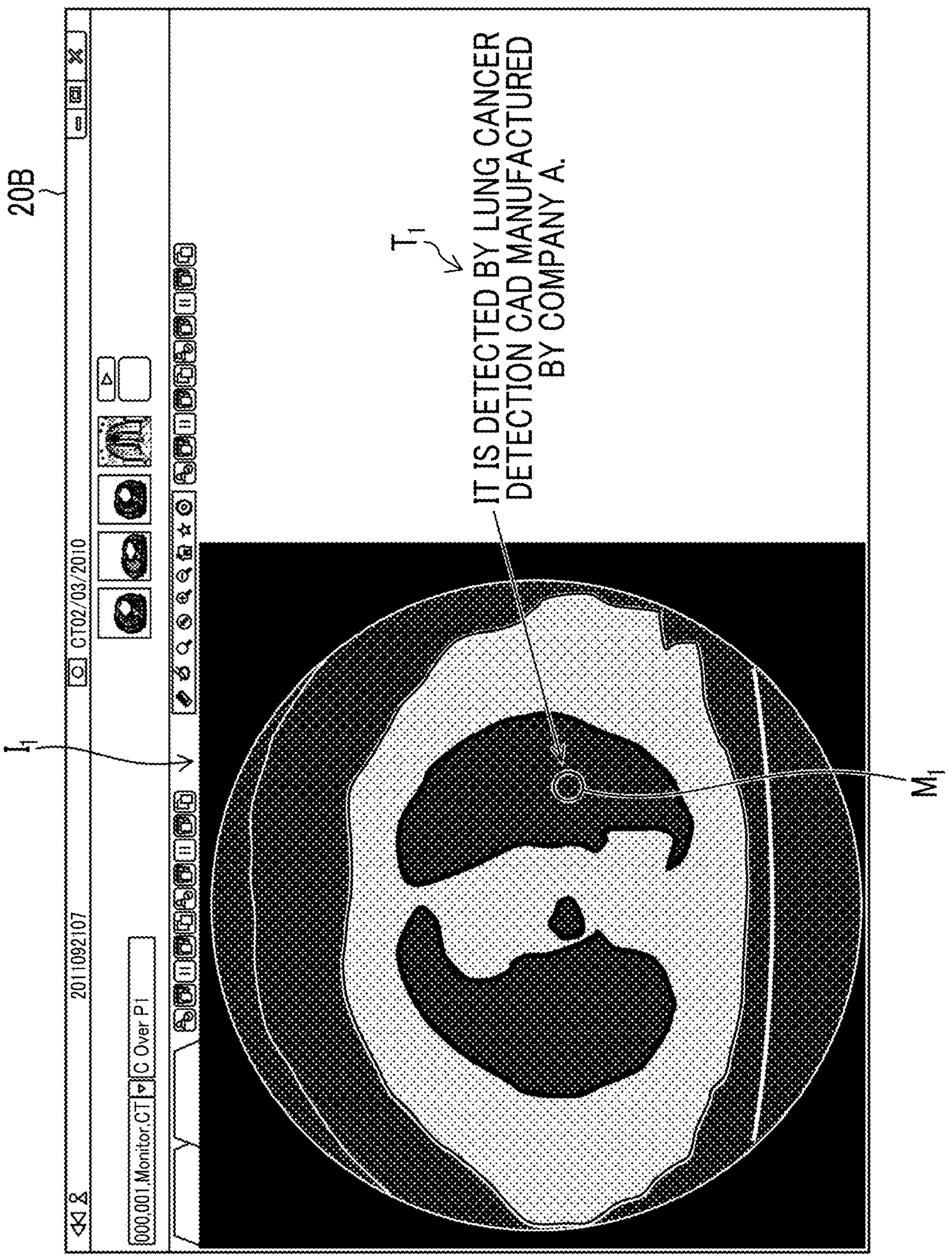
FIG. 4 is a diagram illustrating a display form.

FIG. 4 is a diagram illustrating a display form A. As illustrated in FIG. 4, in the display form A, a CT image $I_1$ is displayed on the display 20B, and a marker $M_1$ surrounding a lesion region of the CT image $I_1$ is superimposed and displayed on the CT image $I_1$. In addition, in the display form A, a description $T_1$ for the CT image $I_1$, which is related to the lesion region surrounded by the marker $M_1$, is displayed in the right region of the CT image $I_1$. Here, the lesion region is detected by the lesion detection AI 16B manufactured by Company A that detects the disease α (lung cancer), and a description $T_1$ "It is detected by lung cancer detection CAD manufactured by Company A." is displayed on the display 20B.

Figure 5:
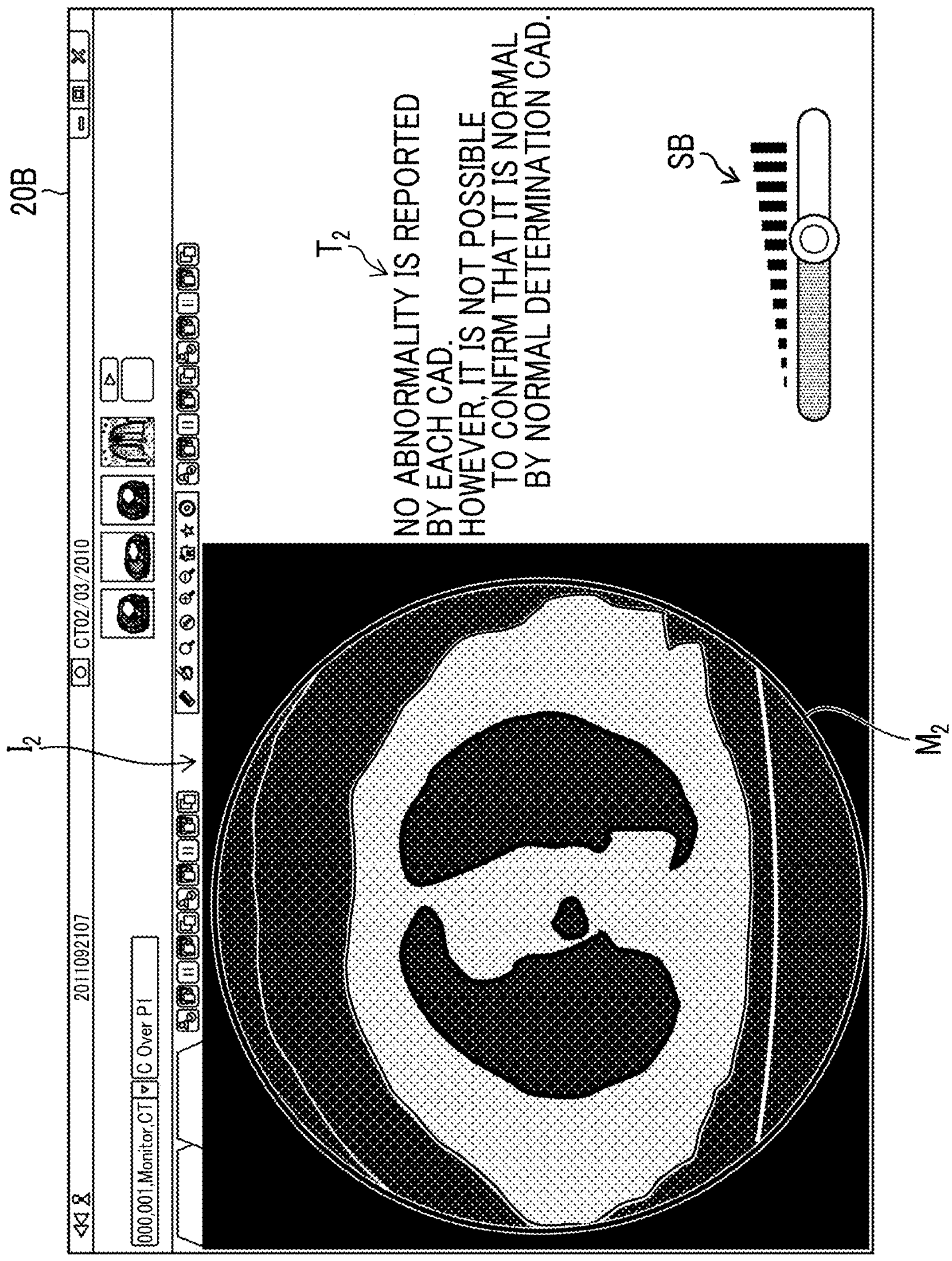
FIG. 5 is a diagram illustrating a display form.

FIG. 5 is a diagram illustrating the display form B. As illustrated in FIG. 5, in the display form B, a CT image $I_2$ is displayed on the display 20B, and a marker $M_2$ surrounding the entire CT image $I_2$ is superimposed and displayed on the CT image $I_2$. In addition, in the display form B, a description $T_2$ for the CT image $I_2$, which is related to the marker $M_2$, is displayed in the right region of the CT image $I_2$. Here, the description $T_2$ "No abnormality is reported by each CAD. However, it is not possible to confirm that the subject is normal by the normal determination CAD." is displayed on the display 20B.

Figure 6:
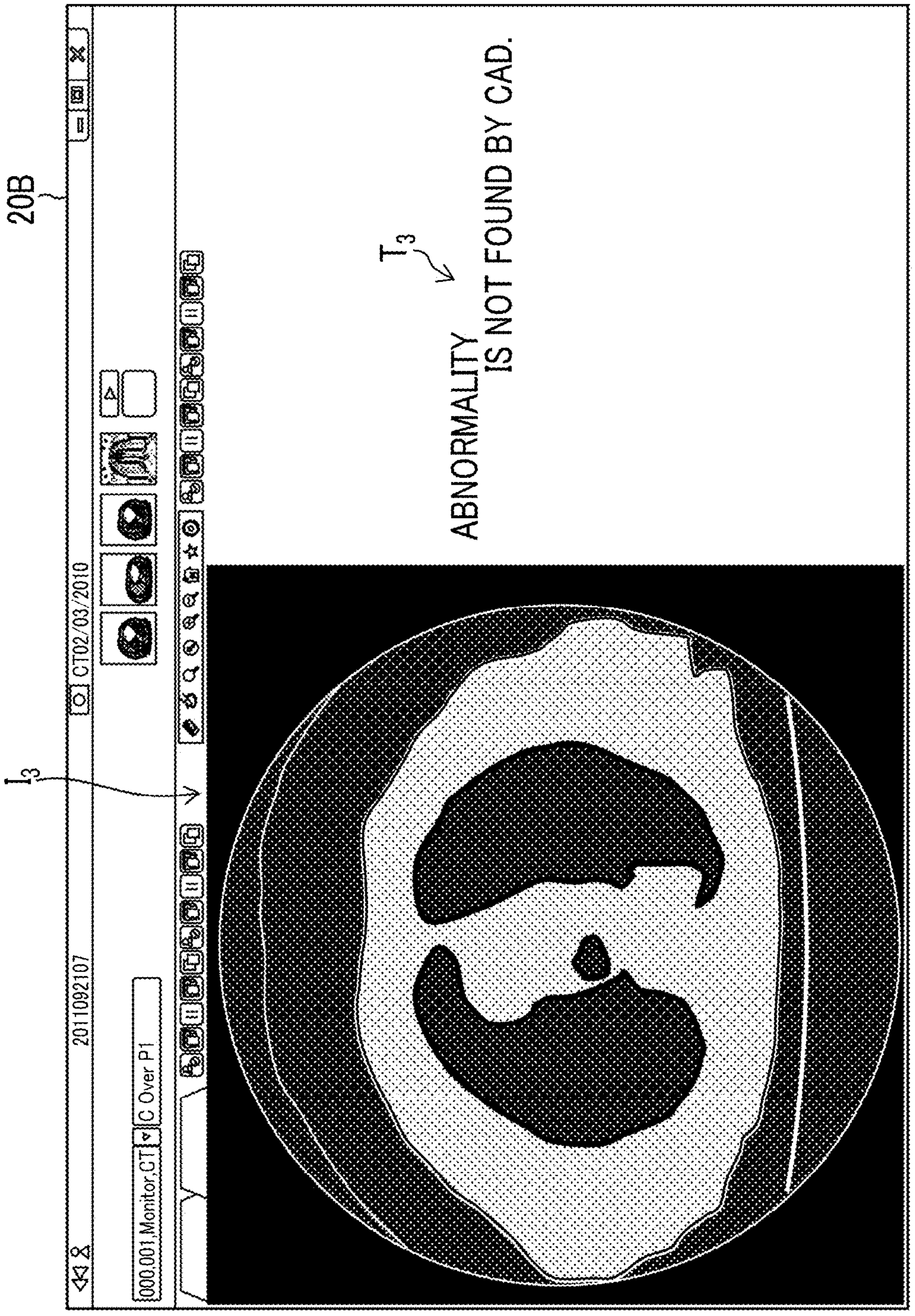
FIG. 6 is a diagram illustrating a display form.

FIG. 6 is a diagram illustrating a display form C. As illustrated in FIG. 6, in the display form C, a CT image $I_3$ is displayed on the display 20B. In addition, in the display form C, a description $T_3$ for the CT image $I_3$ is displayed in a right region of the CT image $I_3$. Here, the description $T_3$ "Abnormality is not found by the CAD." is displayed on the display 20B. Since there is a high probability that the CT image $I_3$ is not abnormal, only a display indicating that the CT image $I_3$ is normal may be performed without displaying the CT image $I_3$, and confirmation by the doctor may be skipped.

In addition, the processor 18B performs post-processing for the respective diagnosis results from the "first determination result" and the "second determination result" differently for the processing form A, the processing form B, and the processing form C in order for the doctor to more simply confirm and determine the diagnosis results and process the medical images.

For example, in the processing form C, a flag that indicates that a check by the doctor may be simple is set, and in the processing form A and the processing form B, the flag is not set. In addition, the display order of the interpretation/examination list for confirming the medical image by the doctor may be changed such that the CT image of processing form A and the CT image of the processing form B are given priority over the CT image of processing form C.

In a case of a health checkup, since it is rare to find an immediate hospitalization or an immediate treatment-level disease, it is possible not to notify the result on the spot, or to report the abnormal finding separately after telling the subject that it is normal. Therefore, for the processing form C, it may be reported on the spot as "no abnormality", and then transfer to processing for collectively confirming whether or not there is really an abnormality later. For example, at the end of one day, the doctor may have a simple check of all the CT images of the processing form C that day. In a case in which an abnormality is found in the simple check, the subject may be separately contacted.

The processor 18B may perform the post-processing differently for the processing form A and the processing form B, respectively.

As described above, according to the medical image diagnosis method, the first determination unit 16A can determine the presence or absence of an abnormality from the medical image. In addition, in a case in which the abnormality is not detected in the first determination unit 16A, it is possible to determine whether the medical image is normal by the second determination unit 18A. Therefore, it is possible to reduce the burden on the doctors in a case in which the image diagnosis is performed on a large number of medical images.

[Others] In a case in which the second determination unit 18A determines that the medical image is not normal, third determination processing of determining the presence or absence of an abnormality from the medical image may be performed. The third determination processing is performed by setting a sensitivity higher than a sensitivity in the first determination processing (a specificity lower than a specificity in the first determination processing), that is, setting the threshold value to be relatively low.

The third determination processing is performed by the first determination unit 16A. The first determination unit 16A performs the third determination processing by setting the sensitivity of each of the lesion detection AIs 16B to 16F to be higher than that in the first determination processing, that is, setting the threshold value to be relatively low. Accordingly, in the third determination processing, a lesion is extracted according to evaluation standards that are acceptable even if something that is not a disease is determined as a disease, and it is reported to the doctor. In a case in which a display form in this case is a display form D, it is desirable to present, to the doctor, that the lesion is extracted by increasing the sensitivity in the display form D.

Figure 7:
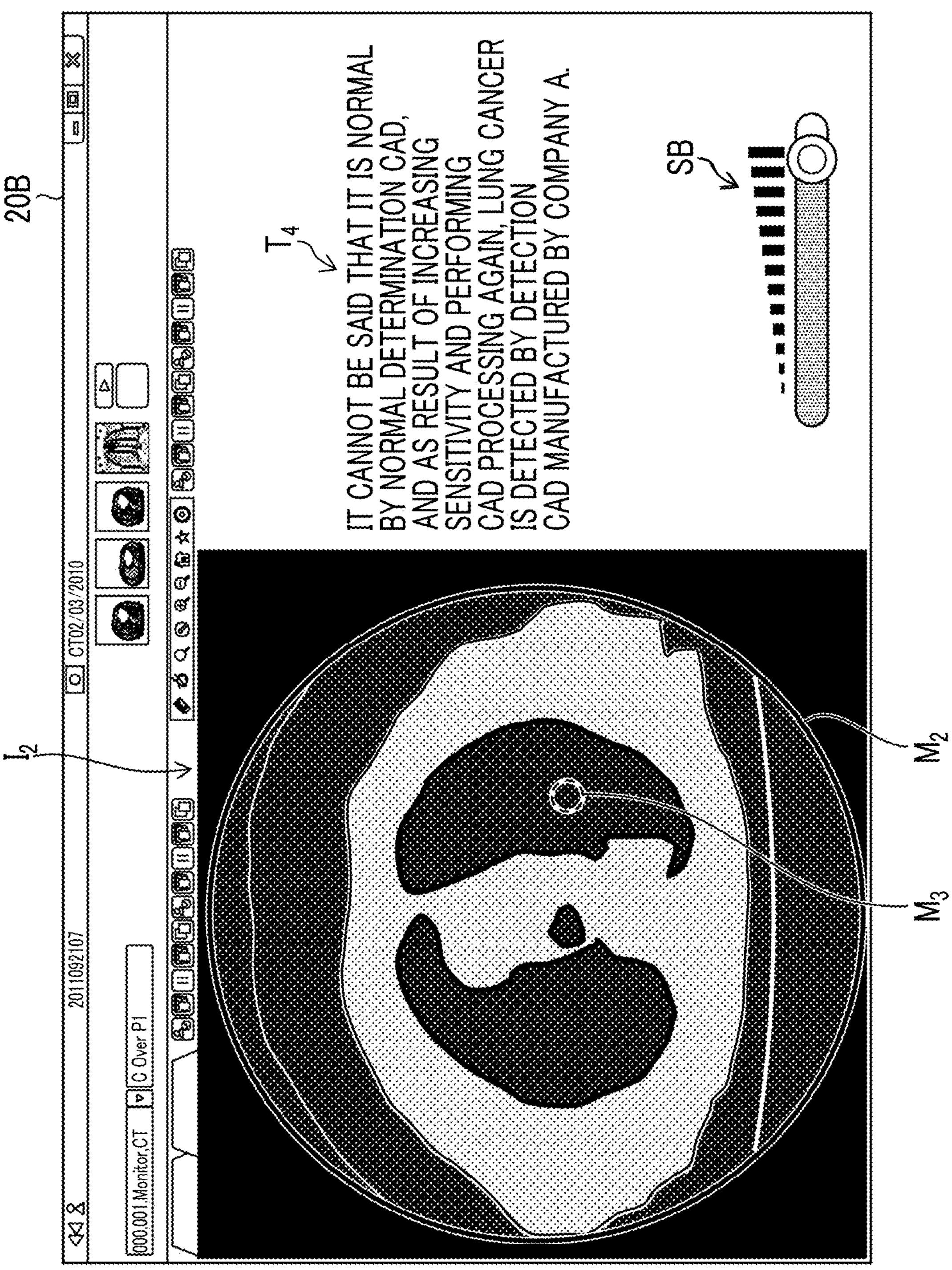
FIG. 7 is a diagram illustrating a display form.

FIG. 7 is a diagram illustrating a display form D. As illustrated in FIG. 7, in the display form D, the CT image $I_2$ is displayed on the display 20B, the marker $M_2$ surrounding the entire CT image $I_2$ is superimposed and displayed on the CT image $I_2$, and a marker $M_3$ surrounding the lesion region of the CT image $I_2$ is further superimposed and displayed on the CT image $I_2$. Unlike the marker $M_1$ of the display form A, the marker $M_3$ is displayed with a broken line to indicate that the lesion is detected by increasing the sensitivity.

In addition, in the display form D, a description $T_4$ for the CT image $I_2$, which is related to the marker $M_3$, is displayed in the right region of the CT image $I_2$. Here, the description $T_4$ "It cannot be said that the subject is normal by the normal determination CAD, and as a result of increasing the sensitivity and performing the CAD processing again, a lung cancer is detected by the detection CAD manufactured by Company A." is displayed on the display 20B.

As illustrated in FIG. 5, a slider bar SB for setting the sensitivity of the first determination unit 16A may be displayed in the display form B. In a case in which the user operates the slider bar SB using the input device 20A to increase the sensitivity, the third determination processing may be performed with the set sensitivity, and the display form may transition to the display form D as illustrated in FIG. 7.

In the present embodiment, although the processing with respect to the CT image of the lung has been described as an example, the present invention is not limited thereto. For example, each of the lesion detection AIs 16B to 16F may extract any one of liver cancer, multiple cysts, liver cirrhosis, or fatty liver from the CT image including the liver.

The technical scope of the present invention is not limited to the scope described in the above-mentioned embodiment. The configurations and the like in each embodiment can be appropriately combined between the respective embodiments without departing from the gist of the present invention.

EXPLANATION OF REFERENCES

10: medical image diagnosis system
12: modality
14: image storage server
16: each company's CAD processing server
16A: first determination unit
16B: lesion detection AI manufactured by Company A
16C: lesion detection AI manufactured by Company A
16D: lesion detection AI manufactured by Company A
16E: lesion detection AI manufactured by Company B
16F: lesion detection AI manufactured by Company C
18: result integration CAD processing server
18A: second determination unit
18B: processor
18C: memory
18D: normal determination AI
20: PACS viewer
20A: input device
20B: display
$I_1$: CT image
$I_2$: CT image
$I_3$: CT image
$M_1$: marker
$M_2$: marker
$M_3$: marker
P1 to P10: each process of medical image diagnosis
S1 to S9: each step of medical image diagnosis
SB: slider bar
$T_1$: description
$T_2$: description
$T_3$: description
$T_4$: description

What is claimed is:

1. A medical image diagnosis system comprising:
at least one processor; and at least one memory that stores a command to be executed by the at least one processor, wherein the at least one processor performs first determination of determining presence or absence of an abnormality from a medical image obtained by imaging a subject, performs second determination of determining whether or not the medical image is normal in a case in which it is determined that the abnormality is absent in the first determination, and performs third determination of determining the presence or absence of the abnormality from the medical image in a case in which it is determined that the medical image is not normal in the second determination, wherein the first determination is performed by a plurality of first trained models, each of the plurality of first trained models detects specific lesion different with each other from the medical image in a case in which the medical image is input, and the first determination determines that the abnormality is present in a case in which the specific lesion is detected by at least one of the plurality of first trained models, the second determination is performed by a second trained model that detects whether any lesion is present from the medical image in a case in which the medical image is input, and the second determination determines that the medical image is not normal in a case in which any lesion is detected by the second trained model, the third determination is performed with a sensitivity relatively higher than a sensitivity in the first determination, and the third determination is performed by the plurality of first trained model, and determines that the abnormality is present in a case in which specific lesion is detected by at least one of the plurality of first trained model.

2. The medical image diagnosis system according to claim 1, wherein, for a first case in which it is determined that the abnormality is present in the first determination, a second case in which it is determined that the abnormality is absent in the first determination and it is determined that the medical image is not normal in the second determination, and a third case in which it is determined that the abnormality is absent in the first determination and it is determined that the medical image is normal in the second determination, the at least one processor displays a diagnosis result of the medical image on a display differently for the third case than for the first and second cases.

3. The medical image diagnosis system according to claim 2, wherein the at least one processor displays the diagnosis result of the medical image on the display differently between the first case and the second case.

4. The medical image diagnosis system according to claim 2, wherein the at least one processor performs different types of post-processing on the medical image for the third case than for the first and second cases.

5. The medical image diagnosis system according to claim 1, wherein the at least one processor performs the first determination and the second determination for each organ of the subject from the medical image.

6. The medical image diagnosis system according to claim 1, wherein the second trained model outputs a probability that the input medical image is normal.

7. The medical image diagnosis system according to claim 1, wherein the second trained model is a trained model that has been trained by using combinations of a normal medical image, an abnormal medical image, and labels indicating whether or not the medical image is normal, as a training data set.

8. A medical image diagnosis method executed by a computer, comprising:

a first determination step of determining presence or absence of an abnormality from a medical image obtained by imaging a subject;

a second determination step of determining whether or not the medical image is normal in a case in which it is determined that the abnormality is absent in the first determination step; and a third determination step of determining the presence or absence of the abnormality from the medical image in a case in which it is determined that the medical image is not normal in the second determination step, wherein the first determination step is performed by a plurality of first trained models, each of the plurality of first trained models detects specific lesion different with each other from the medical image in a case in which the medical image is input, and the first determination step determines that the abnormality is present in a case in which the specific lesion is detected by at least one of the plurality of first trained models, the second determination step is performed by a second trained model that detects whether any lesion is present from the medical image in a case in which the medical image is input, and the second determination step determines that the medical image is not normal in a case in which any lesion is detected by the second trained model, the third determination step is performed with a sensitivity relatively higher than a sensitivity in the first determination step, and the third determination step is performed by the plurality of first trained model, and determines that the abnormality is present in a case in which specific lesion is detected by at least one of the plurality of first trained model.

9. A non-transitory, computer-readable tangible recording medium which records thereon a program for causing, when read by a computer, the a computer to execute the medical image diagnosis method according to claim 8.

* * * * *